(12) United States Patent
Hurst

(10) Patent No.: US 8,303,635 B2
(45) Date of Patent: Nov. 6, 2012

(54) SUPRACHIASMATIC NUCLEUS INDUCING, MELATONIN SUPPRESSING LIGHT EMITTING DEVICE TO ENHANCE WAKE CYCLE

(76) Inventor: Katherine Hurst, Coralville, IA (US)

( * ) Notice: Subject to any disclaimer, the term of this patent is extended or adjusted under 35 U.S.C. 154(b) by 1696 days.

(21) Appl. No.: 11/623,629

(22) Filed: Jan. 16, 2007

(65) Prior Publication Data

US 2008/0170476 A1   Jul. 17, 2008

(51) Int. Cl.
*A61N 5/06* (2006.01)

(52) U.S. Cl. ......................................... 607/88; 128/898

(58) Field of Classification Search .............. 607/88–94; 128/898
See application file for complete search history.

(56) References Cited

U.S. PATENT DOCUMENTS

| | | | |
|---|---|---|---|
| 3,727,395 A * | 4/1973 | Baylor | 368/256 |
| 3,798,889 A * | 3/1974 | Chadwick | 368/73 |
| 4,315,502 A * | 2/1982 | Gorges | 600/27 |
| 4,395,661 A * | 7/1983 | Becker | 315/360 |
| 4,858,609 A * | 8/1989 | Cole | 607/91 |
| 5,046,494 A * | 9/1991 | Searfoss et al. | 607/88 |
| 5,137,018 A * | 8/1992 | Chuprikov et al. | 607/45 |
| 5,176,133 A * | 1/1993 | Czeisler et al. | 607/88 |
| 5,242,376 A * | 9/1993 | Shealy et al. | 600/27 |
| 5,259,830 A * | 11/1993 | Masuda | 600/27 |
| 5,301,090 A * | 4/1994 | Hed | 362/558 |
| 5,304,212 A * | 4/1994 | Czeisler et al. | 607/88 |
| 5,327,331 A * | 7/1994 | Roberts | 362/176 |
| 5,507,716 A * | 4/1996 | LaBerge et al. | 600/27 |
| 6,443,977 B1* | 9/2002 | Jaillet | 607/88 |
| 2001/0056293 A1* | 12/2001 | Brainard | 607/88 |
| 2003/0231495 A1* | 12/2003 | Searfoss, III | 362/251 |
| 2004/0044064 A1* | 3/2004 | Lewy et al. | 514/419 |
| 2005/0012622 A1* | 1/2005 | Sutton | 340/573.1 |
| 2005/0070977 A1* | 3/2005 | Molina | 607/88 |
| 2005/0073839 A1* | 4/2005 | Pederson et al. | 362/230 |
| 2005/0179392 A1* | 8/2005 | Waumans et al. | 313/639 |
| 2005/0185399 A1* | 8/2005 | Beermann et al. | 362/231 |
| 2005/0248962 A1* | 11/2005 | Searfoss, III | 362/642 |
| 2006/0009822 A1* | 1/2006 | Savage et al. | 607/88 |
| 2006/0064144 A1* | 3/2006 | Chen et al. | 607/90 |
| 2007/0118026 A1* | 5/2007 | Kameyama et al. | 600/300 |
| 2009/0134819 A1* | 5/2009 | Noguchi et al. | 315/308 |

OTHER PUBLICATIONS

The Human Circadian Pacemaker Can See by the Dawn's Early Light, Danilenko et al.; Journal of Biological Rhythms, Oct. 2000.*

* cited by examiner

*Primary Examiner* — Henry M Johnson, III
(74) *Attorney, Agent, or Firm* — Hogan Lovells US LLP

(57) ABSTRACT

A light emitting device to awaken an animal and stimulate the Suprachiasmatic Nucleus in the brain to suppress melatonin secretion. The device can be programmed for an initiation time, color of light, brightness, frequency of pulsating light, and level of gradual intensity. It has the advantage of being silent and does not to disturb other people sleeping in the same room.

5 Claims, 7 Drawing Sheets

SUPRACHIASMATIC NUCLEUS INDUCING, MELATONIN SUPPRESSING LIGHT EMITTING DEVICE TO ENHANCE WAKE CYCLE

BACKGROUND OF THE INVENTION

People have been waking up virtually the same way for over 225 years. A desired time to wake up is set and then a loud, irritating often-repetitive, sound is used to awaken the person. Seth Thomas Clock Company was granted a patent in 1876 for a small bedside alarm clock. Technology has made this system a bit easier but the stimulus to wake up remains highly unchanged since the patent was first granted. In 1876, the alarm clock was a fabulous way to indicate when to rise from sleep since sound was easy to produce and it worked. However, a great amount of work on the brain and how sensory information is processed has been conducted since 1876.

Although sound was an excellent way to wake someone up in 1876, studies of the brain and sensory system has shown sound has absolutely nothing to do with the regulation of sleep and wake cycles, and therefore the use of sound to awaken somebody from sleep is an antiquated method for the $21^{st}$ century.

The brain has been designed to quickly receive and process information relayed by sound due to its importance in the survival of the species. The auditory cortex in the human brain is the special area used to process sound. The auditory cortex allows communication between and among humans. Language is processed there and speech is also initiated there. The auditory cortex has nothing to do with sleep wake cycles.

Studies of the wake/sleep cycle have demonstrated an interesting and wonderful system for its regulation—light. The light is sensed by the eyes and travels on the second cranial nerve (optic nerve) to a nucleus in the brain called the suprachiasmatic nucleus. When light intensity is low, the suprachiasmatic nucleus signals the pineal gland to produce a hormone called melatonin, which causes the feeling of drowsiness. When light intensities are high, the production of melatonin is inhibited.

The suprachiasmatic nucleus system is so sophisticated that even people who are blind still respond to changes in light intensity through melatonin level fluctuations. This supports a separate tract for the sensory input and response to light stimulus for regulating the sleep/wake cycle.

Human physiology and behavior is dominated by near-24-hour rhythms that have a major impact on our health and well-being. For example, alertness and performance patterns, core body temperature rhythms and the production of hormones, such as, melatonin and cortisol are all regulated by an endogenous near-24-hour oscillator in the suprachiasmatic nuclei (SCN) of the anterior hypothalamus. Light information is captured by specialized retinal photoreceptors and sent directly to the SCN along a dedicated neural pathway, the retinohypothalamic tract (RHT). The intensity, number, duration, pattern and timing of exposure to light, as well as, the wavelength of light have been shown to regulate to circadian resetting. The human brain is extremely sensitive to dim light. A light intensity equivalent to indoor room light is able to significantly effect changes in hormone release. The wavelength of the light is important in humans with an increased sensitivity to short wavelength light and spectral sensitivity which is different from conventional scotopic and photopic vision.

It is inevitable, even though light is the correct stimulus to awaken a person, for a desensitization to occur over time. Adaption to a stimulus eventually occurs so it must be changed in order to be effective. If a person sets a device at a frequency, color and/or intensity, it may wake them up very well for a while, but in a few months or years, they may sleep right through the light stimulus. Alarms clocks can be loud and annoying but people sleep right through them because their brain has adapted to the stimulus.

Additionally, a light stimulus does what sound cannot, decrease melatonin. This is the hormone that causes lethargy and sleepiness. People hate early morning because they feel sleepy and tired. They feel this way because they woke up with a system that does not depress the levels of melatonin.

The pineal gland synthesizes and secretes melatonin, a hormone that communicates information about environmental lighting to various parts of the body. Melatonin has the ability to entrain biological rhythms and has important effects on reproductive function of many animals.

The pineal gland is a small organ shaped like a pine cone. The pineal gland is composed of "pinealocytes" and glial cells. It is located on the midline, attached to the posterior end of the roof of the third ventricle in the brain.

The precursor to melatonin is serotonin, a neurotransmitter that itself is derived from the amino acid tryptophan. Synthesis and secretion of melatonin is dramatically affected by light exposure to the eyes. The fundamental pattern observed is that serum concentrations of melatonin are low during the daylight hours, and increase to a peak during the dark. The circadian rhythm in melatonin secretion in humans is that blood levels of melatonin are essentially undetectable during daytime, but rise sharply during the dark. Other species have very similar patterns. The duration of melatonin secretion each day is directly proportional to the length of the night.

Melatonin has important effects in integrating photoperiod and affecting circadian rhythms. Consequently, it has been reported to have significant effects on reproduction, sleep-wake cycles and other phenomena showing circadian rhythm.

Seasonal changes in day length have profound effects on reproduction in many species, and melatonin is a key player in controlling such events. In temperate climates, animals like hamsters, horses and sheep have distinct breeding season. During the non-breeding season, the gonads become inactive (e.g., males fail to produce sperm in any number), but as the breeding season approaches, the gonads must be rejuvenated. Photoperiod—the length of day vs. night—is the most important cue allowing animals to determine which season it is. The pineal gland is able to measure day length and adjust secretion of melatonin accordingly.

The effect of melatonin on reproductive systems can be summarized by saying that it is anti-gonadotropic. In other words, melatonin inhibits the secretion of the gonadotropic hormones luteinizing hormone and follicle-stimulating hormone from the anterior pituitary. Much of this inhibitory effect seems due to inhibition of gonadotropin-releasing hormone from the hypothalamus, which is necessary for secretion of the anterior pituitary hormones. One practical application of melatonin's role in controlling seasonal reproduction is found in its use to artificially manipulate cycles in seasonal breeders.

The disclosed light emitting device is different from other devices that appear similar, although only superficially. There are products that use a face covering to block out light and may play music or other sounds to sooth the person into sleep or induce a perceived good sleep experience. Although these devices may appear similar, they are meant to function in the opposite of the disclosed light emitting device in that they are trying to make a person sleep better, while the disclosed device is meant to awaken a person from sleep.

There are some devices that have a face covering and emit light from the face covering to modify the circadian rhythm in a person. These devices, although emitting light, are not worn when sleeping or used to awaken a person like an alarm clock but instead are meant to combat jet lag or fatigue, or to increase beta-endorphins in the bloodstream of the subject.

The disclosed light emitting device takes advantage of the modern discoveries in medicine and brain physiology. The device allows a subject to awaken from sleep at a predetermined time, while achieving a reduction in drowsiness.

BRIEF SUMMARY OF THE INVENTION

The light emitting device is meant to replace the conventional alarm clock. Sound is not used at all, this alarm is silent. A person can program the mask with a desired wake up time, color of light, brightness, frequency of pulsating light, and level of gradual intensity. It has been shown that a pulsating light is the best stimulus to depress melatonin levels in humans. A preferred method is a pulsating light of a wavelengths 450-460 nm. The importance of a pulsating light has only recently been discovered as a factor in melatonin production. The disclosed device is able to depress melatonin slowly over time to a comfortable level to make early mornings become productive and pleasant.

The disclosed device combines physiology, neuroscience, endocrinology, evolutionary biology, engineering, and research to produce a new and improved alarm system.

The disclosed device can be used by anybody to avoid oversleeping. Mornings are more productive when a person does not feel drowsy or tired. Additionally, it has the added advantage of being silent so as not to disturb other people sleeping in the same room as usually caused by loud alarm clock. A spouse or roommate can comfortably sleep beside a person who has to wake up at 5:00 AM without being bothered. The disclosed device can have a lens that plane polarizes the light and cuts out UV light for comfort and safety. The disclosed device is safe to use during sleep since no wires or external output are needed when used as a face covering.

The disclosed device can use any source for the producing the correct light wavelengths and pulses. The use of an LED as the light source has several advantages. An LED is a low energy, high output device and reduces the need for replacing burned out units. An LED light source can produce light of varying intensity, wavelength and pulsate rate. The energy needs are very low so it can be powered by batteries and still function for long periods. A small computer can be included with the disclosed device so no external input is required. A menu or display allows a person to personalize their wake up alarm. The system can have memory so a person can save an awake routine. The disclosed device, in one design, can be a mask worn while a person is sleeping and easily removed in the morning. The mask is soft and fits over the eyes. The computer unit can be imbedded into the mask and programmed to send the wake up signal or shut off.

The mask can have a foam case that is lightweight and comfortable. The light source or LED can be embedded deep in the foam so the person does not feel them. However, the foam allows the light source or LED to create a bright light to stimulate properly the user.

The controls (control center) and power source can be included in the mask and covered with soft material. After being programmed, they can be hidden to allow the user to sleep comfortable.

The user can adjust the awakening sequence (initiation, duration, pulse rate, wave length, intensity, etc,) to obtain a routine that best suits them. The disclosed device can have other designs using the same principles of preprogrammed pulsating light—a pillow or pillow case, a device next to the bed (e.g., table, bed post, head board, etc.), a device hanging on the wall, or a device located in any place used for sleeping so the light enters the eye. A well-fitted mask would be the best way to deliver the light but other alternates are possible as well.

DETAILED DESCRIPTION OF THE INVENTION

The disclosed device uses pulses of light directed at the eyes of a subject to awaken them from sleep. Although the device can be in any design or format that accomplishes the needed impulses to simulate a subject from sleep, a mask is a preferred design. The mask has a band to attach the mask to the face of the user. The shape of the mask is designed to house the electronics, fit comfortably, block light from outside and be stylish. Various materials can be used to make the mask. The material should be sturdy, lightweight, durable, and block light. The side of the mask facing the user can have a light weight, soft foam that rests against the user. The foam has holes for the light source, and plane polarizing, UV light blocking lenses, which provides a distance from mask and eyes, and comfort for the user. The mask can be used with or without the control center. The control center can be easily removed from the mask when it needs to be replaced due to wear and tear. A replacement mask will accept the original control center and the original worn out mask can be thrown away.

A LED array made of a variety of colors is arranged and connected to a logic chip. The logic chip is able to program the array to turn on at a set time, and have a specific color, pulsation rate, and intensity. The chip will have memory to save routines. The chip also may provide a random surprise wake up signal with unknown color, intensity and pulsation rate. A battery source, a screen, and connections to all components will be housed in the control center. The case will be made from a light weight material. The control center is able to be separated from the mask. The case can be opened for programming and easily closed after programming.

An alternative to the mask design of the disclosed device is a pillow unit with the previously described components. The foam is large enough the fit inside a typical pillow case and the control center is covered to protect its electronic components. The electronics is housed within the pillow with the LEDs embedded in the pillow. The LEDs are covered with a plane polarizing UV light blocking lens, if needed.

Another alternative design to the disclosed device is a bedside apparatus. It can be attached to a head board on a bed or on a nearby table.

Figure 1:
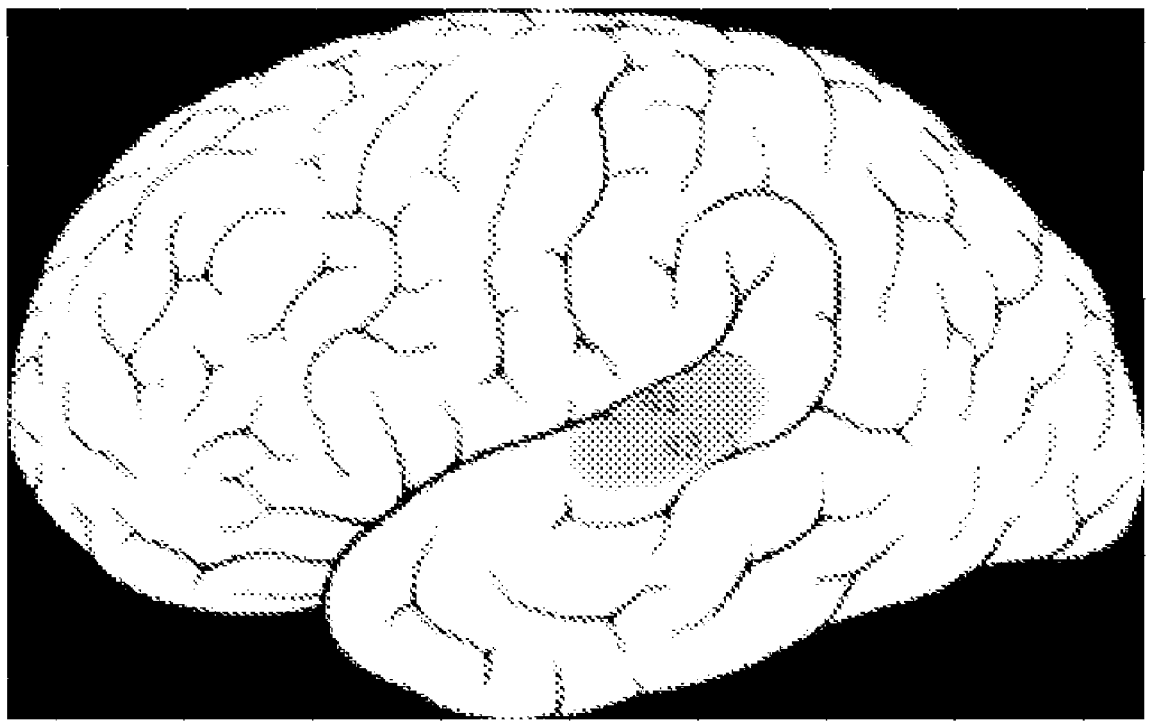
FIG. 1 illustrates the area [auditory cortex] in the human brain used to process the sense of sound.
Figure 2:
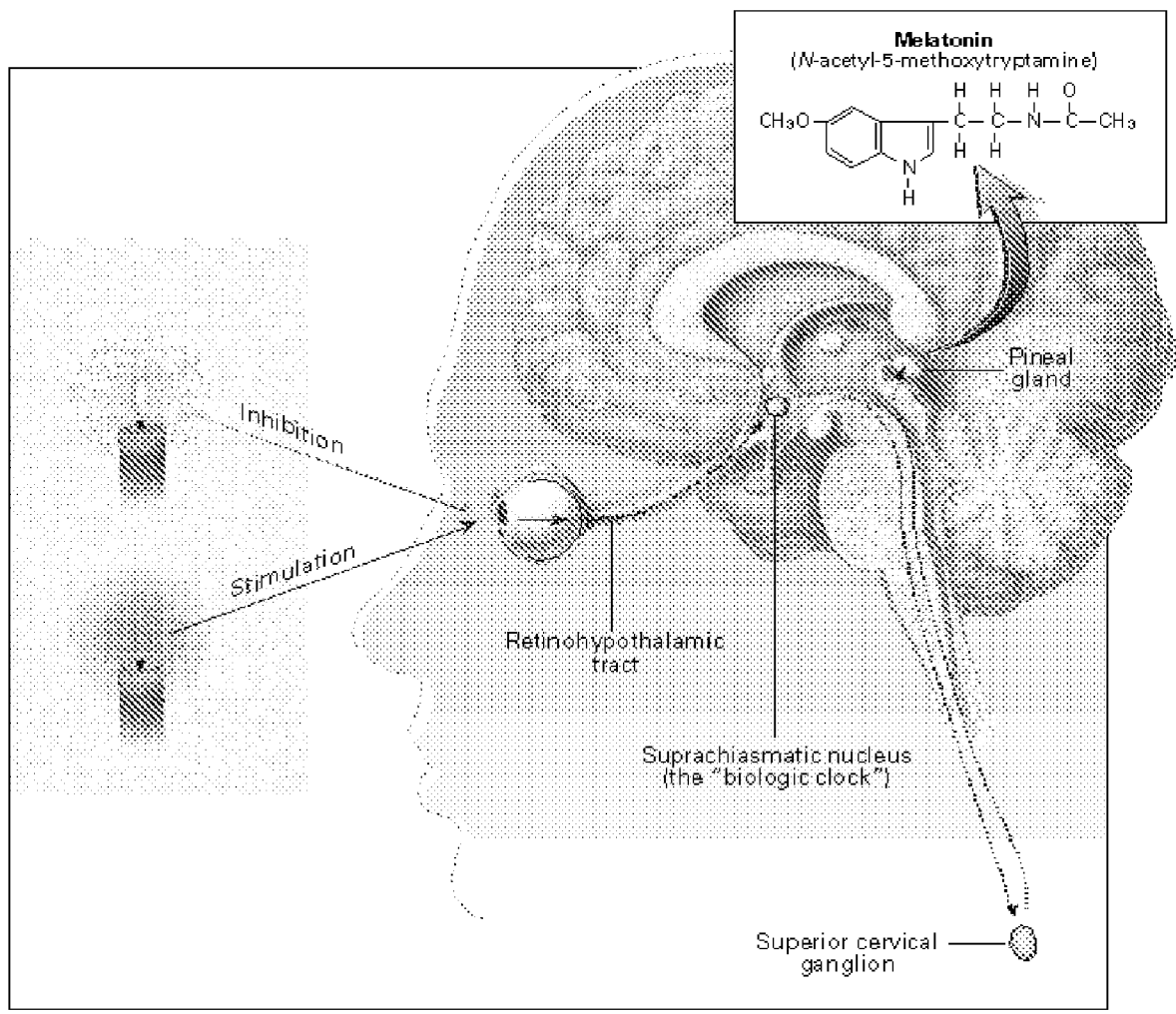
FIG. 2 illustrates the suprachiasmatic nucleus in the human brain and physiology of melatonin secretion (Brzezinski A., N Engl J Med, 1997, 336:186-195).
Figure 3:
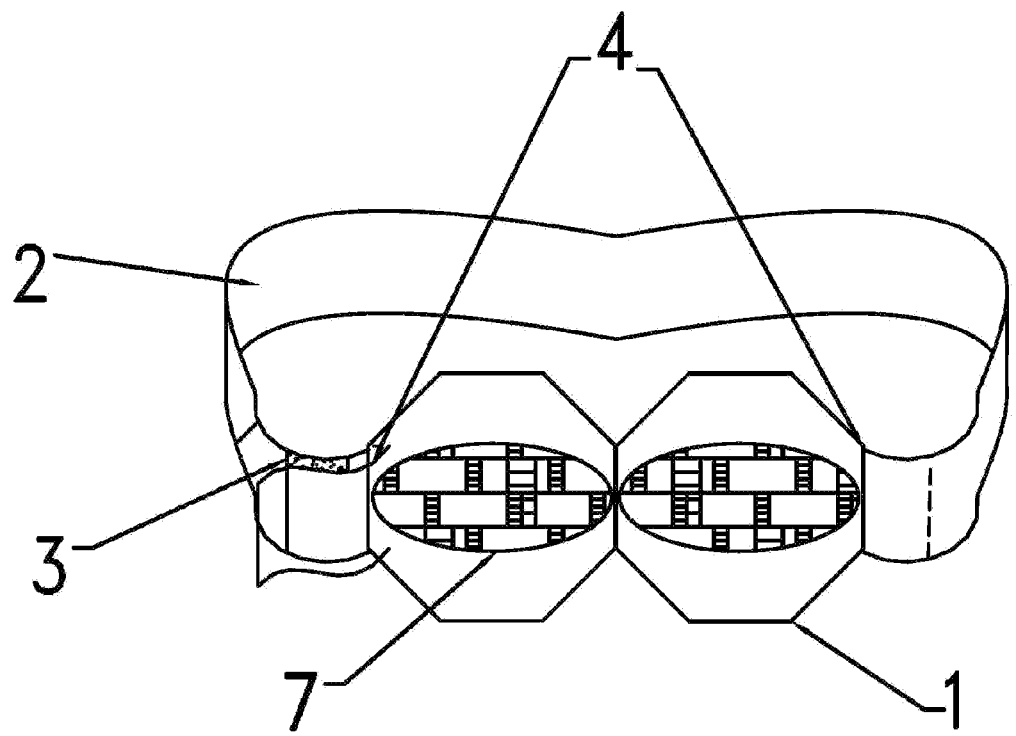
FIG. 3 illustrates the light emitting device as a face mask.

FIG. 3 shows the light emitting device as a face mask with the band 2 connected to the mask 1 by a loop 4 passing through the mask 1. The end of the band is retained by an attachment site 3. Contained within the mask 1 is a case 7.

Figure 4:
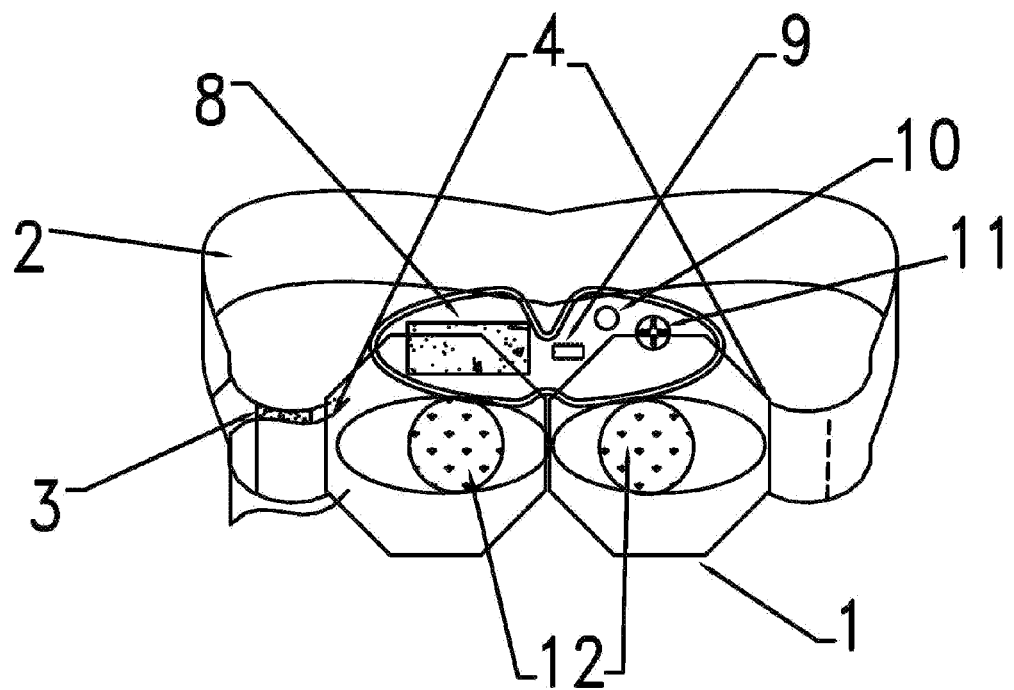
FIG. 4 illustrates the light emitting device as a face mask with the case containing the controls (control center) and display open during use.

FIG. 4 shows the light emitting device as a face mask with the case 7 flipped open to show the contents. The case 7 has on the top cover a screen 8, a logic chip 9, a battery 10, and the controls (control center) 11. The mask 1 has the light source arrays 12 underneath the case 7 cover.

Figure 5:
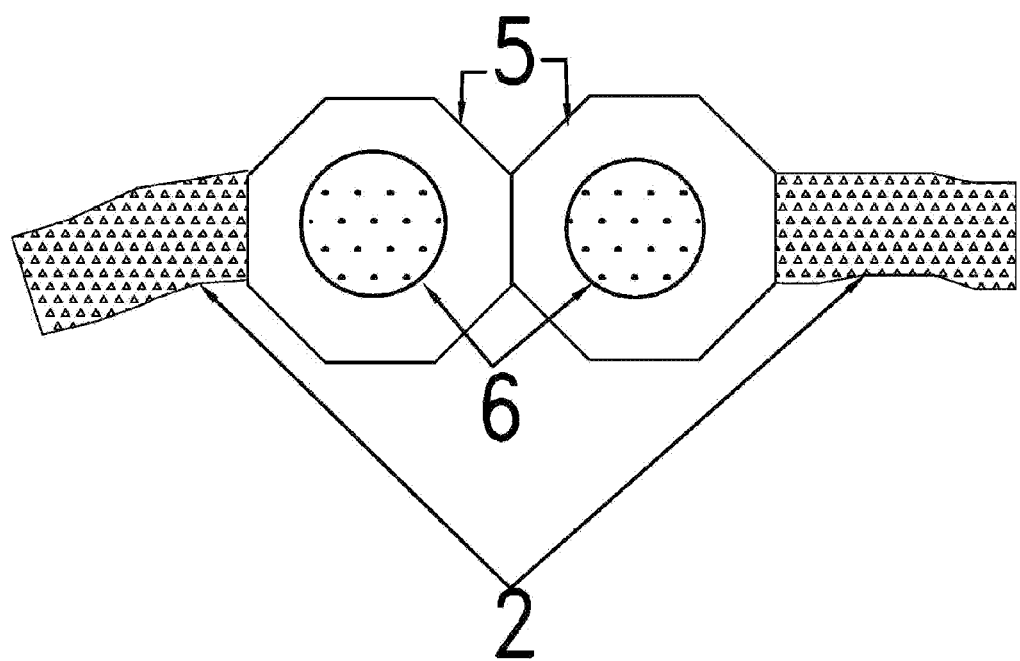
FIG. 5 illustrates the inner surface (surface contacting the face) face mask version of the light emitting device.

FIG. 5 shows the light emitting device as a face mask with the inside (surface touching face) of mask 1. The inside of the mask 1 has a layer of soft material or foam 5. Over the area where the person's eyes would be located are lenses 6.

Figure 6:
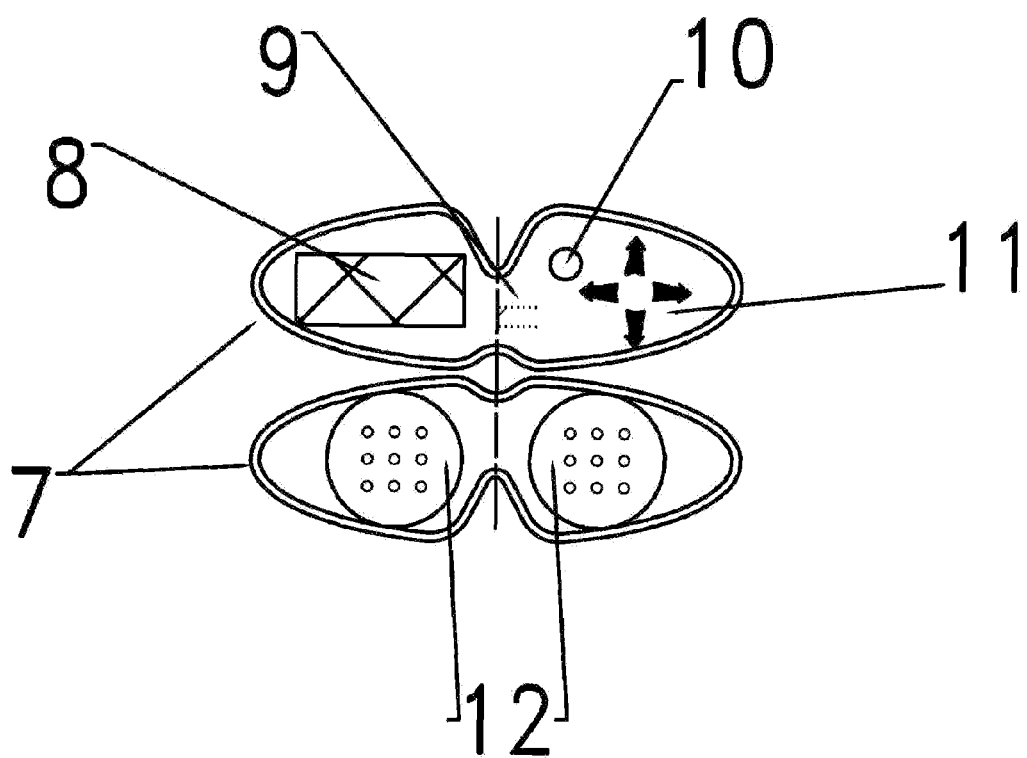
FIG. 6 illustrates the case containing the controls (control center) and display.

FIG. 6 shows a close-up of the case 7. The top of the cover has the screen 8, logic chip 9, battery 10, and controls (control center) 11. The bottom of the case 7 has the light source arrays 12.

Figure 7:
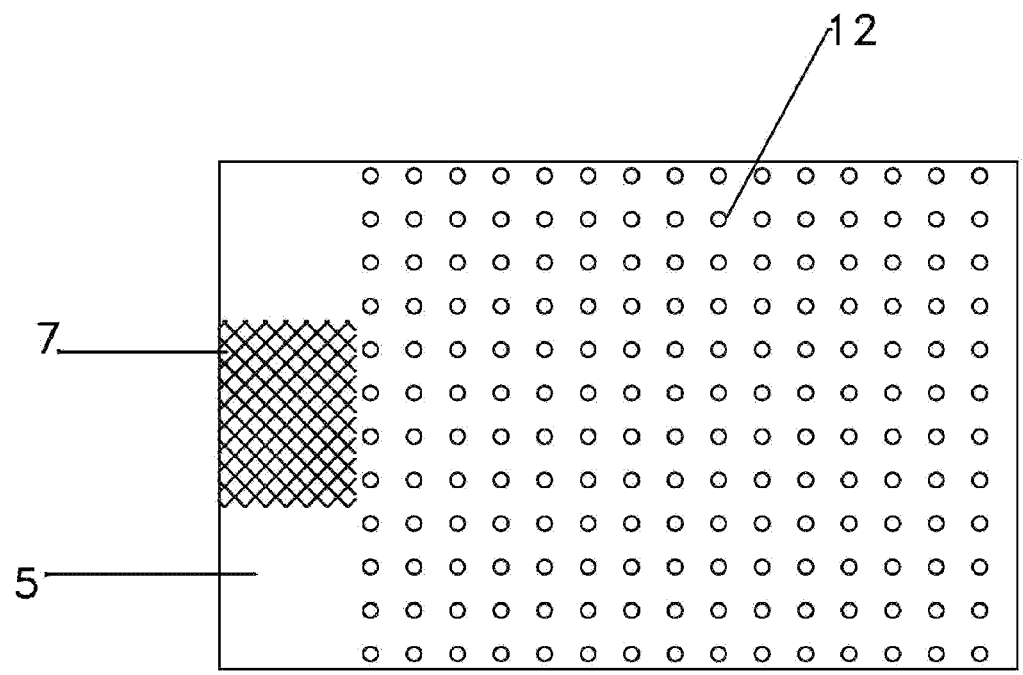
FIG. 7 illustrates a pillow containing the controls (control center) and display.

FIG. 7 shows the light emitting device as a pillow covered with a layer of soft material or foam 5. The pillow has a case 7 containing the controls (control center) that regulates the light source arrays 12 on the outside of the pillow.

Embodiments

In one embodiment the device is a face covering device. In another embodiment the device is a mask. In another embodiment the device is a shield. In another embodiment the device is a free-standing device. In another embodiment the device is a lamp. In another embodiment the device is a pillow case. In another embodiment the device is wall-mounted device. In another embodiment the device is a pair of glasses. In another embodiment the device is a television. In another embodiment the device is a plasma screen. In another embodiment the device is a LCD screen.

In one embodiment the band is elastic. In another embodiment the band is cloth. In another embodiment the band is plastic. In another embodiment the band is a string. In another embodiment the band is rubber. In another embodiment the band is a cord. In another embodiment the band is a flexible material.

In one embodiment the attachment is VELCRO™ (generic: hook and loop fastener). In another embodiment the attachment is adhesive. In another embodiment the attachment is a buckle. In another embodiment the attachment is a sliding clasp. In another embodiment the attachment is a knot. In another embodiment the attachment is a button. In another embodiment the attachment is a snap. In another embodiment the attachment is a hook.

In one embodiment the inner surface of the face covering is foam. In another embodiment the inner surface of the face covering is cloth.

In one embodiment the lenses are glass. In another embodiment the lenses are plastic. In another embodiment the lenses are filters to select the proper wave length of light.

In one embodiment the light source is a light bulb. In another embodiment the light source is a light emitting diode (LED). In another embodiment the light sources is a liquid crystal display (LCD). In another embodiment the light source is a plasma display. In another embodiment the light source is a multi-frequency light source with a filter.

In one embodiment the controls are digital. In another embodiment the controls are analog. In another embodiment the controls are toggles. In another embodiment the controls are push buttons.

In one embodiment the timer is electronic. In another embodiment the timer is mechanical. In another embodiment the timer is external from the device. In another embodiment the timer is external from the device.

In one embodiment the initiation of the awakening series of events is by a timer. In another embodiment the initiation of the awakening series of events is by an external electronic signal. In another embodiment the initiation of the awakening series of events is by a pager. In another embodiment the initiation of the awakening series of events is by a phone call. In another embodiment the initiation of the awakening series of events is by a cell phone call. In another embodiment the initiation of the awakening series of events is by an e-mail.

In one embodiment the light emitting device awakens an animal. In another embodiment the light emitting device awakens a mammal. In another embodiment the light emitting device awakens a pet. In another embodiment the light emitting device awakens dog or cat. In another embodiment the light emitting device awakens domestic animals. In another embodiment the light emitting device awakens a commercial production of animal. In another embodiment the light emitting device awakens a pig, cow, or chicken. In another embodiment light emitting device awakens a primate. In another embodiment light emitting device awakens a human.

In one embodiment the light emitting device stimulates hormone production in an animal. In another embodiment the light emitting device stimulates hormone production in a mammal. In another embodiment the light emitting device stimulates hormone production in a pet. In another embodiment the light emitting device stimulates hormone production in dog or cat. In another embodiment the light emitting device stimulates hormone production in domestic animals. In another embodiment the light emitting device stimulates hormone production in a commercial production of animal. In another embodiment the light emitting device stimulates hormone production in a pig, cow, or chicken. In another embodiment light emitting device stimulates hormone production in a primate. In another embodiment light emitting device stimulates hormone production in a human.

In one embodiment the light emitting device inhibits hormone production in an animal. In another embodiment the light emitting device inhibits hormone production in a mammal. In another embodiment the light emitting device inhibits hormone production in a pet. In another embodiment the light emitting device inhibits hormone production in dog or cat. In another embodiment the light emitting device inhibits hormone production in domestic animals. In another embodiment the light emitting device inhibits hormone production in a commercial production of animal. In another embodiment the light emitting device inhibits hormone production in a pig, cow, or chicken. In another embodiment light emitting device inhibits hormone production in a primate. In another embodiment light emitting device inhibits hormone production in a human.

In one embodiment the light emitting device has a power source. In another embodiment the light emitting device has an external power source. In another embodiment the light emitting device has an internal power source. In another embodiment the light emitting device has a DC current power source. In another embodiment the light emitting device has an AC power source. In another embodiment the light emitting device has a battery power source.

In one embodiment the light source of the light emitting device emits a light of any wave length from 400 to 700 nm. In another embodiment the light source of the light emitting device emits a light of a wave length between 400 and 650 nm.

In another embodiment the light source of the light emitting device emits a light of a wave length between 400 and 600 nm. In another embodiment the light source of the light emitting device emits a light of a wave length between 400 and 550 nm. In another embodiment the light source of the light emitting device emits a light of a wave length between 400 and 500 nm. In another embodiment the light source of the light emitting device emits a light of a wave length between 425 and 475 nm. In another embodiment the light source of the light emitting device emits a light of a wave length between 430 and 470 nm. In another embodiment the light source of the light emitting device emits a light of a wave length between 440 and 465 nm. In another embodiment the light source of the light emitting device emits a light of a wave length between 450 and 460 nm. In another embodiment the light source of the light emitting device emits a light of a wave length of 450 nm. In another embodiment the light source of the light emitting device emits a light of a wave length of 460 nm.

In one embodiment the light source of the light emitting device emits a light pulse at a rate between 600 pulses/minute to 2 pulses/hour. In another embodiment the light source of the light emitting device emits a light pulse at a rate between 300 pulses/minutes to 4 pulses/hour. In another embodiment the light source of the light emitting device emits a light pulse at a rate between 120 pulses/minutes to 12 pulses/hour. In another embodiment the light source of the light emitting device emits a light pulse at a rate between 60 pulses/minute to 60 pulses/hour. In another embodiment the light source of the light emitting device emits a light pulse at a rate between 30 pulses/minute to 2 pulses/minute. In another embodiment the light source of the light emitting device emits a light pulse at a rate between 20 pulses/minute to 3 pulses/minute. In another embodiment the light source of the light emitting device emits a light pulse at a rate between 10 pulses/minute to 4 pulses/minute. In another embodiment the light source of the light emitting device emits a light pulse at a rate between 8 pulses/minute to 5 pulses/minute.

In one embodiment the light source of the light emitting device emits a light of any intensity from 0 and 4,000 lux. In one embodiment the light source of the light emitting device emits a light of an intensity between 0 and 4,000 lux. In another embodiment the light source of the light emitting device emits a light of an intensity between 50 and 3,000 lux. In another embodiment the light source of the light emitting device emits a light of an intensity between 100 and 2,000 lux. In another embodiment the light source of the light emitting device emits a light of an intensity between 150 and 1,000 lux. In another embodiment the light source of the light emitting device emits a light of an intensity between 150 and 500 lux. In another embodiment the light source of the light emitting device emits a light of an intensity between 150 and 450 lux. In another embodiment the light source of the light emitting device emits a light of an intensity between 150 and 400 lux. In another embodiment the light source of the light emitting device emits a light of an intensity between 150 and 250 lux. In another embodiment the light source of the light emitting device emits a light of an intensity 150 lux.

Other Embodiments

It is to be understood that while the invention has been described in conjunction with the detailed description thereof, the foregoing description is intended to illustrate and not limit the scope of the invention, which is defined by the scope of the appended claims. For example, although the above description relates to humans, various aspects of the invention might also be applied to other animals (e.g., chicken, mice, rats, cows, sheep, monkeys, apes, horses, goats, cats, dogs, pigs, etc.) by making appropriate modifications to the described methods. Other aspects, advantages, and modifications are within the scope of the following claims.

The invention claimed is:

1. A method of awakening an animal, comprising:
    a. programming a controller for a light emitting device to emit the light at a selected time, wave length, pulse rate and intensity,
    b. emitting the light from the light emitting device at the selected time,
    c. emitting the light from the light emitting device at the selected wave length from 400 nm to 700 nm,
    d. emitting the light from the light emitting device at the selected pulse rate from 600 pulses/minute to 2 pulses/hour,
    e. emitting the light from the light emitting device at the selected intensity from 0 lux to 4,000 lux,
    f. exposing the animal to the light from the light emitting device, and
    g. awakening the animal.

2. The method of claim 1, wherein the controller for the light emitting device does not control the pulse rate and the light emitting device emits light pulses at a pre-determined pulse rate.

3. The method of claim 1, wherein the controller for the light emitting device does not control the light wave length and the light emitting device emits light at a pre-determined wave length range.

4. The method of claim 1, wherein the controller for the light emitting device does not control the light intensity and the light emitting device emits light with a pre-determined intensity.

5. The method of claim 1, wherein the light emitting device emits a light with an intensity that is gradually increased from zero to maximum value.

* * * * *